US011826363B2

(12) United States Patent
Takayama et al.

(10) Patent No.: US 11,826,363 B2
(45) Date of Patent: Nov. 28, 2023

(54) THERAPEUTIC AGENT FOR SOLID CANCERS, WHICH COMPRISES AXL INHIBITOR AS ACTIVE INGREDIENT

(71) Applicants: ONO PHARMACEUTICAL CO., LTD., Osaka (JP); KYOTO PREFECTURAL PUBLIC UNIVERSITY CORPORATION, Kyoto (JP)

(72) Inventors: Koichi Takayama, Kyoto (JP); Tadaaki Yamada, Kyoto (JP); Tomoko Yasuhiro, Osaka (JP); Kohei Tanaka, Osaka (JP)

(73) Assignees: ONO PHARMACEUTICAL CO., LTD., Osaka (JP); KYOTO PREFECTURAL PUBLIC UNIVERSITY CORPORATION, Kyoto (JP)

( * ) Notice: Subject to any disclaimer, the term of this patent is extended or adjusted under 35 U.S.C. 154(b) by 0 days.

(21) Appl. No.: 16/754,266

(22) PCT Filed: Oct. 12, 2018

(86) PCT No.: PCT/JP2018/038202
§ 371 (c)(1),
(2) Date: Apr. 7, 2020

(87) PCT Pub. No.: WO2019/074116
PCT Pub. Date: Apr. 18, 2019

(65) Prior Publication Data
US 2020/0330453 A1  Oct. 22, 2020

(30) Foreign Application Priority Data
Oct. 13, 2017 (JP) .................. 2017-199598

(51) Int. Cl.
*A61K 31/4709* (2006.01)
*A61P 35/00* (2006.01)
*A61K 31/506* (2006.01)

(52) U.S. Cl.
CPC .......... *A61K 31/4709* (2013.01); *A61P 35/00* (2018.01); *A61K 31/506* (2013.01)

(58) Field of Classification Search
CPC ................................. A61K 31/4709
USPC ...................................... 514/312
See application file for complete search history.

(56) References Cited

U.S. PATENT DOCUMENTS

| | | | |
|---|---|---|---|
| 9,562,060 B2 | 2/2017 | Cheng et al. | |
| 9,573,935 B2 | 2/2017 | Inukai et al. | |
| 9,994,549 B2 | 6/2018 | Inukai et al. | |
| 10,208,022 B2 | 2/2019 | Inukai et al. | |
| 10,501,442 B2 | 12/2019 | Inukai et al. | |
| 10,836,747 B2 | 11/2020 | Nekado et al. | |
| 2002/0048610 A1 | 4/2002 | Cima et al. | |
| 2007/0060613 A1 | 3/2007 | Kim | |
| 2008/0312232 A1 | 12/2008 | Kim et al. | |
| 2009/0274693 A1 | 11/2009 | Gilmer et al. | |
| 2009/0306103 A1 | 12/2009 | Boyer et al. | |
| 2009/0324587 A1 | 12/2009 | Goodwin et al. | |
| 2011/0053931 A1 | 3/2011 | Gaudino et al. | |
| 2011/0092503 A1 | 4/2011 | Ullrich et al. | |
| 2011/0118252 A1 | 5/2011 | Kim et al. | |
| 2012/0070413 A1 | 3/2012 | Kim et al. | |
| 2012/0230991 A1 | 9/2012 | Graham et al. | |
| 2013/0142790 A1 | 6/2013 | Gilmer et al. | |
| 2013/0150363 A1 | 6/2013 | Gilmer et al. | |
| 2014/0018365 A1 | 1/2014 | Schultz-Fademrecht et al. | |
| 2014/0121126 A1 | 5/2014 | Bivona et al. | |
| 2014/0206679 A1 | 7/2014 | Cheng et al. | |
| 2014/0275077 A1 | 9/2014 | Dandu et al. | |
| 2016/0168121 A1* | 6/2016 | Inukai | A61P 37/02 514/235.2 |
| 2017/0088542 A1 | 3/2017 | Inukai et al. | |
| 2019/0099413 A1 | 4/2019 | Tanaka et al. | |
| 2019/0389837 A1 | 12/2019 | Nekado et al. | |

FOREIGN PATENT DOCUMENTS

| | | |
|---|---|---|
| CN | 101528702 A | 9/2009 |
| CN | 102083824 A | 6/2011 |
| CN | 103124729 A | 5/2013 |
| EP | 3 575 293 A1 | 12/2019 |
| JP | 2003-519698 A | 6/2003 |
| JP | 2008-539275 A | 11/2008 |
| JP | 2009-519242 A | 5/2009 |
| JP | 2009-537632 A | 10/2009 |
| JP | 2009-539878 A | 11/2009 |
| JP | 2010-178651 A | 9/2010 |

(Continued)

OTHER PUBLICATIONS

AstraZeneca, (2015) Tagrisso (Osimertinib) Prescribing Information.*
"Regulations on Fixed-Dose Combination and Co-Packaged Drug and/or Biological Products" Department of Health and Human Services(HHS), 2015, p. 1 (1page total).
Office Action dated Mar. 24, 2021, issued by the India Intellectual Property Office in Indian Patent Application No. 201647002406.
U.S. Patent Office, Non-Final Office Action dated Oct. 31, 2019, issued in U.S. Appl. No. 16/540,306.

(Continued)

Primary Examiner — Taofiq A Solola
(74) Attorney, Agent, or Firm — Sughrue Mion, PLLC

(57) ABSTRACT

A therapeutic agent for treatment of solid cancers, including, as an effective component, N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt in combination with osimertinib or a pharmaceutically acceptable salt thereof. The combination of the present invention has strong antitumor effect and is therefore useful for treatment of solid cancers.

3 Claims, No Drawings

(56) References Cited

FOREIGN PATENT DOCUMENTS

| | | |
|---|---|---|
| JP | 2011-517689 A | 6/2011 |
| JP | 2014-533287 A | 12/2014 |
| RU | 2 240 313 C2 | 11/2004 |
| WO | 01/30758 A1 | 5/2001 |
| WO | 2006/116713 A1 | 11/2006 |
| WO | 2007/033196 A1 | 3/2007 |
| WO | 2007/146824 A2 | 12/2007 |
| WO | 2008/035209 A2 | 3/2008 |
| WO | 2008/048375 A1 | 4/2008 |
| WO | 2009/137429 A1 | 11/2009 |
| WO | 2009/140549 A1 | 11/2009 |
| WO | 2010/039248 A1 | 4/2010 |
| WO | 2012/011548 A1 | 1/2012 |
| WO | 2012/028332 A1 | 3/2012 |
| WO | 2012/080729 A2 | 6/2012 |
| WO | 2013/074633 A1 | 5/2013 |
| WO | 2015/012298 A1 | 1/2015 |
| WO | 2016/193680 A1 | 12/2016 |
| WO | 2017/146236 A1 | 8/2017 |

OTHER PUBLICATIONS

U.S. Patent Office, Notice of Allowance dated Jan. 29, 2020, issued in U.S. Appl. No. 16/540,306.
U.S. Patent Office, Non-Final Office Action dated Feb. 18, 2020, issued in U.S. Appl. No. 16/079,823.
U.S. Patent Office, Non-Final Office Action dated May 6, 2016, issued in U.S. Appl. No. 14/906,993.
U.S. Patent Office, Notice of Allowance Action dated Sep. 12, 2016, issued in U.S. Appl. No. 14/906,993.
U.S. Patent Office, Non-Final Office Action dated Sep. 15, 2017, issued in U.S. Appl. No. 15/373,091.
U.S. Patent Office, Non-Final Office Action dated Jan. 17, 2018, issued in U.S. Appl. No. 15/373,091.
U.S. Patent Office, Non-Final Office Action dated Jun. 21, 2018, issued in U.S. Appl. No. 15/975,999.
U.S. Patent Office, Notice of Allowance dated Oct. 10, 2018, issued in U.S. Appl. No. 15/975,999.
U.S. Patent Office, Non-Final Office Action dated Feb. 6, 2019, issued in U.S. Appl. No. 16/237,275.
U.S. Patent Office, Final Office Action dated May 23, 2019, issued in U.S. Appl. No. 16/237,275.
U.S. Patent Office, Notice of Allowance dated May 30, 2019, issued in U.S. Appl. No. 16/237,275.
U.S. Patent Office, Second Notice of Allowance dated Aug. 23, 2019, issued in U.S. Appl. No. 16/237,275.
International Searching Authority, Search Report dated Aug. 19, 2014 in International Patent Application No. PCT/JP2014/069419 (PCT/ISA/210).
International Searching Authority, Written Opinion dated Aug. 19, 2014 in International Patent Application No. PCT/JP2014/069419 (PCT/ISA/237).
State Intellectual Property Office of the People's Republic of China, Communication dated Nov. 2, 2016 issued in Chinese Patent Application No. 201480041780.2.
European Patent Office, Extended European Search Report dated Dec. 6, 2016, in European Application No. 14828976.2.
International Searching Authority, Search Report dated Feb. 9, 2016 in International Patent Application No. PCT/JP2015/086050 (PCT/ISA/210).
International Searching Authority, Written Opinion dated Feb. 9, 2016 in International Patent Application No. PCT/JP2015/086050 (PCT/ISA/237).
European Patent Office, Extended European Search Report dated Nov. 15, 2017, in European Application No. 15873185.1.
International Searching Authority, Search Report dated Mar. 20, 2018, in International Patent Application No. PCT/JP 2018/002250 (PCT/ISA/210).
International Searching Authority, Search Report dated Nov. 6, 2018, in International Patent Application No. PCT/JP 2018/031047 (PCT/ISA/210).
International Searching Authority, Written Opinion dated Nov. 6, 2018, in International Patent Application No. PCT/JP 2018/031047 (PCT/ISA/237).
International Searching Authority, Search Report dated Apr. 4, 2017, in International Patent Application No. PCT/JP 2017/007219 (PCT/ISA/210).
International Searching Authority, Written Opinion dated Apr. 4, 2017, in International Patent Application No. PCT/JP 2017/007219 (PCT/ISA/237).
European Patent Office, Extended European Search Report issued on Nov. 8, 2018, in European Application No. 17756670.0.
V.A. Korshunov; "Axl-dependent signalling: a clinical update", 2012 Biochemical Society, Clinical Science (2012) vol. 122, pp. 361-368.
C. Gjerdrum et al., "Axl is an essential epithelial-to-mesenchymal transition-induced regulator of breast cancer metastasis and patient survival", Proceedings of the National Academy of Sciences of the United States of America, Jan. 19, 2010, vol. 107, No. 3, pp. 1124-1129. (6 pages total).
Il-Kyoo Park et al., "Inhibition of the receptor tyrosine kinase Axl impedes activation of the FLT3 internal tandem duplication in human acute myeloid leukemia: implications for Axl as a potential therapeutic target", Blood Journal, Mar. 14, 2013, vol. 121, No. 11. (11 pages total).
Douglas K. Graham et al., "The TAM family: phospatidylscrine-sensing receptor tyrosine kinases gone awry in cancer", Nature Reviews Cancer, vol. 14, Nov. 24, 2014, pp. 769-785. (1 page total).
"BG8324 Enhances Immune Checkpoint Inhibitor Efficacy in Preclinica.L Cancer Models" BerGenBio AS, Sep. 21, 2015 (url:htps://www.bergenbio.com/bgb324-enhances-immunecheckpoint-inhibitor-efficacy-in-preclinical-cancer-models/ [retrieved Feb. 12, 2020] (Year: 2015) (1 page).
Gro Gausdal et al. "Abstract B014: BGB324, a selective small molecule inhibitor of the receptor tyrosine kinase AXL, enhances immune checkpoint inhibitor efficacy" Cancer Immunology Research, CRI-CIMTEATI-AACR Inaugural International Cancer Immunotherapy Conference: Translating Science into Survival, Sep. 16-19, 2015, (pp. 1-4).
Registry (STN) [online], Jan. 16, 2001, RN 314026-41-0, [retrieval date Aug. 6, 2014], Total 1 page.
Zhang, et al.; "Discovery of novel type II c-Met inhibitors based on BMS-777607", European Journal of Medicinal Chemistry, vol. 80, Apr. 2014, 13 pages total.
Lovering, et al.; "Identification of Type-II Inhibitors Using Kinase Structures", Chemical Biology and Drug Design, vol. 80, No. 5, Jun. 2012, 8 pages total.
Bhattacharya et al: "Identification of novel series of pyrazole and indole-urea based DFGout PYK2 inhibitors", Bioorganic & Medicinal Chemistry Letters, vol. 22, No. 24, Dec. 1, 2012, XP05509390, pp. 7523-7529, (7 pages total).
Allen G et al. "Identification of small molecule inhibitors of proline-rich tyrosine kinase 2 (Pyk2) with osteogenic activity in osteoblast cells", Bioorganic & Medicinal Chemistry Letters, vol. 19, No. 17, Sep. 1, 2009, XP026458526, pp. 4924-4928, (5 pages total).
Rothlin et al. "TAM receptor signaling and autoimmune disease", Current Opinion in Immunology, vol. 22 2010, (pp. 740-746).
Linger et al. "TAM Receptor Tyrosine Kinases: Biologic Functions, Signaling, and Potential Therapeutic Targeting in Human Cancer", Advances in Cancer Research, 2008, (pp. 35-83).
Anette Fiebeler et al. "Growth Arrest Specific Protein 6/Axl Signaling in Human Inflammatory Renal Diseases" American Journal of Kidney Disease, vol. 43, No. 2, Feb. 2004, (pp. 286-295).
Rothlin et al. "TAM Receptor Signaling in Immune Homeostasis" American review of Immunology, vol. 33, Jan. 14, 2015, (pp. 355-391).
Zhihui Wang et al. "Mathematical modeling in cancer drug discovery" Drug Discovery Today, vol. 19, No. 2, Feb. 2014, (pp. 145-150).

(56) References Cited

OTHER PUBLICATIONS

Marelli et al. "Tumor targeting via integrin ligands" Frontiers in Oncology, vol. 3, Article 222, Aug. 30, 2013, (pp. 1-12).
T. Fujimori et al. "The Axl receptor tyrosine kinase is a discriminator of macrophage function in the inflamed lung" Mucosal Immunology, vol. 8, No. 5, Sep. 2015, (pp. 1021-1030).
Zagórska et al. Diversification of TAM receptor tyrosine kinase function Nature Immunology vol. 15, No. 10, Oct. 2014, (pp. 920-930).
VandenBrink et al. "Evaluation of CYP2C8 Inhibition in Vitro: Utility of Montelukast as a Selective CYP2C8 Probe Substrate" The American Society for Pharmacology and Experimental Therapeutics, vol. 31, No. 9, 2011, (p. 1546-1554).
Berge et al., "Pharmaceutical Salts", Journal of Pharmaceutical Sciences, vol. 66, No. 1, Jan. 1977, pp. 1-19, 19 pages total.
Kawaguchi et al., "Drug and crystal polymorphism", Journal of Human Environmental Engineering, vol. 4, No. 2, 2002, pp. 310-317, 10 pages total.
Specifications and Test Methods of New Pharmaceuticals, PFSB / ELD Notification, No. 568, 2001, 25 pages total.
Ooshima, "Crystallization of Polymorphs and Pseudo-polymorphs and Its Control", Pharm Stage, vol. 6, No. 10, 2007, pp. 48-53, 9 pages total.
Takata, "API form screening and selection in drug discovery stage", Pharm Stage, vol. 6, No. 10, 2007, pp. 20-25, 10 pages total.
Yamano, "Approach to Crystal Polymorph in Process Research of New Drug", Synthetic Organic Chemistry, vol. 65, No. 9, 2007, pp. 907-913, 11 pages total.
Byrn et al., "Pharmaceutical Solids: A Strategic Approach to Regulatory Considerations", Pharmaceutical Research, vol. 12, No. 7, 1995, pp. 945-954, 10 pages total.
Wnuk-Lipinska, Katarzyna et al., "Abstract B:30: Selective small molecule AXL inhibitor BGB324 overcomes acquired drug resistance in non-small cell lung carcinoma models", Clinical Cancer Research, the American Association for Cancer Research [online] Jan. 2014, vol. 20, No. 2, Supplement, Abstract B30.
Kanakura, Yuzuru, "Guideline for tumors of hematopoietic and lymphoid tissues of the Japanese Society of Hematology", Japanese Society of Hematology, Oct. 2013 (292 pages total).
Kuniko Sunami, "CTLA-4 o Hyoteki to shita Gan Men'eki Ryoho", Japanese Journal of Clinical Medicine (special extra issue) Saishin Gan Yakubutsu Ryohogaku, Feb. 20, 2014, vol. 72, Suppl. 2, pp. 280-285. (8 pages total).
Shin Foong Ngiow et al., "Anti-TIM3 Antibody Promotes T Cell IFN-ɤ -Mediated Antitumor Immunity and Suppresses Established Tumors", Cancer Research, May 15, 2011, vol. 71, No. 10, pp. OF1-OF12. (13 pages total).
Christine Pasero et al., "Interfering with coinhibitory molecules: BTLA/HVEM as new targets to enhance anti-tumor immunity", Immunology Letters, Jan. 8, 2013, vol. 151, pp. 71-75, (5 pages total).
Patrick A. Ott, "CTLA-4 and PD-1/PD-L1 Blockade: New Immunotherapeutic Modalities with Durable Clinical Benefit in Melanoma Patients", Clinical Cancer Research, vol. 19, No. 19, Oct. 1, 2013, pp. 5300-5309 (12 pages total), P55458362.
Xiaoliang Wu et al. "AXL kinase as a novel target for cancer therapy" Oncotarget, vol. 5, No. 20, Oct. 16, 2014, (pp. 9546-9563).
Yoshizawa et al., "Abstract LB-218: Development of Axl/Mer inhibitor, ONO-9330547: preclinical evidence supporting the combination with immunotherapeutics", Cancer Research, Jul. 2016. (2 pages total).
Final Office Action dated Jul. 13, 2020 by the USPTO in U.S. Appl. No. 16/079,823.
Myers et al., "AXL Inhibitors in Cancer: A Medicinal Chemistry Perspective", Journal of Medicinal Chemistry, vol. 59, 2016, pp. 3593-3608, 16 pages total.
Cogle et al., "Oral Azacitidine (CC-486) for the Treatment of Myelodysplastic Syndromes and Acute Myeloid Leukemia", The Oncologist, vol. 20, 2015, pp. 1404-1412, 9 pages total.
Yang et al., "Afatinib versus cisplatin-based chemotherapy for EGFR mutation-positive lung adenocarcinoma (LUX-Lung 3 and LUX-Lung 6): analysis of overall survival data from two randomised, phase 3 trials", The Lancet, vol. 16, 2015, pp. 141-151, 11 pages total.

* cited by examiner

THERAPEUTIC AGENT FOR SOLID CANCERS, WHICH COMPRISES AXL INHIBITOR AS ACTIVE INGREDIENT

TECHNICAL FIELD

The present invention, in one aspect, relates to a therapeutic agent for solid cancers including an Axl inhibitor as an effective component and to be administered in combination with osimertinib, wherein the Axl inhibitor is N-{5-[(6,7-dimethoxy-4-quinoliny)oxy]-2-pyridinyl}-2,5-dioxo-1-phenyl-1,2,5,6,7,8-hexahydro-3-quinolinecarboxamide (hereinafter also abbreviated as a "compound A"), a pharmaceutically acceptable salt thereof, or a hydrate of the compound or the salt.

BACKGROUND ART

Axl (also known as: UFO, ARK, Tyro7) is a receptor tyrosine kinase belonging to a TAM family (Axl, Mer, and Tyro3) cloned from tumor cells. Gas6 (growth-arrest-specific protein 6) cloned as a gene specifically expressed at the time of cell proliferation arrest is known as a ligand for Axl. Axl activated by binding of Gas6 transfers a signal via phosphorylation. Since the signal activates an Erk1/2 pathway or a PI3K/Akt pathway, the activation of Axl is known to be involved in pathologic conditions of cancers, immune system diseases, circulatory system diseases, and the like (see Non-Patent Literature 1).

In particular, the relation between Axl and various types of cancers is well known. For example, it is known that the expression of Axl is involved in metastasis and prognosis of breast cancer (see Non-Patent Literature 2), and that Axl is involved in the pathologic conditions of acute myeloid leukemia (AML) (see Non-Patent Literature 3). Furthermore, it is reported that a TAM family including Axl is expressed in immunocytes such as dendritic cells or macrophages, and suppressively regulates anti-tumor immunization (see Non-Patent Literature 4). Therefore, it is considered that compounds inhibiting the activation of Axl are useful for treatment of various types of cancers, immune system diseases, and circulatory system diseases.

Patent Literature 1 discloses that a compound A has an Axl inhibitory effect and is useful as an agent for cancer treatment (see Patent Literature 1).

Patent Literature 2 discloses that a combination of a compound represented by the general formula (I) and an immune checkpoint inhibitor is useful for cancer treatment (see Patent Literature 2).

CITATION LIST

Patent Literatures

[Patent Literature 1] International Publication WO2015/012298
[Patent Literature 2] International Publication WO2017/146236

Non-Patent Literature

[Non-Patent Literature 1] Clinical Science, Vol. 122, p. 361-368, 2012
[Non-Patent Literature 2] Proceedings of the National Academy of Sciences of the United States of America, Vol. 107, No. 3, p. 1124-1129, 2010
[Non-Patent Literature 3] Blood, Vol. 121, p. 2064-2073, 2013
[Non-Patent Literature 4] Nature Reviews Cancer, Vol. 14, p. 769-785, 2014

SUMMARY OF INVENTION

Technical Problem

An object of the present invention is to find an effective method for treating solid cancers and to provide the method in the form of a pharmaceutical product.

Solution to Problem

In order to solve the above-mentioned problem, the present inventors have keenly studied. As a result, the present inventors have found that the above-mentioned problem can be solved by a combination of an Axl inhibitor as a compound A, a pharmaceutically acceptable salt thereof, or a hydrate of the compound or the salt with osimertinib or a pharmaceutically acceptable salt thereof (hereinafter also abbreviated as the combination of the present invention).

The present invention provides, for example, the following embodiments.

[1] A therapeutic agent for solid cancers comprising an Axl inhibitor as an effective component and to be administered in combination with osimertinib or a pharmaceutically acceptable salt thereof, wherein the Ax inhibitor is N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt,

[2] the agent according to the above [1], wherein the solid cancers include head and neck cancer, nasopharyngeal cancer, esophageal cancer, gastro-esophageal junction cancer, esophageal adenocarcinoma, stomach cancer, large-intestine cancer, colon cancer, rectum cancer, small-intestine cancer, anal cancer (for example, anal canal cancer), liver cancer (for example, hepatocellular carcinoma), gallbladder cancer, bile duct cancer, biliary tract cancer, pancreatic cancer, thyroid cancer, parathyroid cancer, lung cancer (for example, non-small cell lung cancer (for example, squamous non-small cell lung cancer, non-squamous non-small cell lung cancer), small cell lung cancer), breast cancer, ovarian cancer (for example, serous ovarian cancer, ovarian clear cell adenocarcinoma), fallopian tube cancer, uterine cancer (for example, cervical cancer, uterine body cancer, endometrial cancer), vaginal cancer, vulvar cancer, penile cancer, kidney cancer (for example, renal cell carcinoma, clear cell renal cell carcinoma), adrenal cancer, urothelial carcinoma (for example, urinary bladder cancer, upper urinary tract cancer, ureteral cancer, renal pelvic cancer, and urethral cancer), prostate cancer, testicular tumor (for example, germ cell tumor), bone and soft tissue sarcoma (for example, Ewing's sarcoma, childhood rhabdomyosarcoma, and uterine body leiomyosarcoma), skin cancer (for example, uveal malignant melanoma, malignant melanoma (for example, malignant melanoma in the skin, oral mucoepithelium or intraorbital, etc.), Merkel cell carcinoma), glioma (for example, glioblastoma, gliosarcoma), brain tumor (for example, glioblastoma), spinal tumor, Kaposi's sarcoma, squamous cell carcinoma, pleural mesothelioma, primary peritoneal cancer, endocrine cancer, childhood cancer, or cancer of unknown primary origin,

[3] the agent according to the above [1] or [2], wherein the solid cancer is pancreatic cancer, lung cancer, or skin cancer,

[4] the agent according to any one of the above [1] to [3], wherein the solid cancer is lung cancer,

[5] the agent according to the above [4], wherein the lung cancer is EGFR gene exon 19 deletion mutation-positive lung cancer,

[6] the agent according to the above [5], wherein the EGFR gene exon 19 deletion mutation-positive lung cancer is EGFR inhibitor highly sensitive lung cancer,

[7] the agent according to the above [4], wherein the lung cancer is EGFR inhibitor-resistant lung cancer,

[8] the agent according to the above [7], wherein the EGFR inhibitor-resistant lung cancer is gefitinib-resistant lung cancer,

[9] the agent according to the above [7], wherein the EGFR inhibitor-resistant lung cancer is EGFR T790M mutation-positive lung cancer,

[10] the agent according to any one of the above [3] to [9], wherein the lung cancer is non-small cell lung cancer,

[11] A method for treating solid cancers, the method including administering an effective amount of N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt in combination with osimertinib or a pharmaceutically acceptable salt thereof to a patient in need of treatment of solid cancer,

[12] a method for treating solid cancers, the method including administering an effective amount of N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt to a patient, wherein the patient is being treated with osimertinib or a pharmaceutically acceptable salt thereof,

[13] N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt to be used in combination with osimertinib or a pharmaceutically acceptable salt thereof for treatment of solid cancers,

[14] use of N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt for manufacturing a therapeutic agent for solid cancers to be administered in combination with osimertinib or a pharmaceutically acceptable salt thereof,

[15] a therapeutic agent for solid cancers including osimertinib or a pharmaceutically acceptable salt thereof as an effective component and to be administered in combination with an Axl inhibitor, wherein the Axl inhibitor is N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt,

[16] a pharmaceutical composition for treatment of solid cancers to be administered in combination with an Axl inhibitor and osimertinib or a pharmaceutically acceptable salt thereof, wherein the Axl inhibitor is N-{5-[(6, 7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt,

[17] a combination of N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt with osimertinib or a pharmaceutically acceptable salt thereof to be used for treatment of solid cancers,

[18] use of a combination of N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt with osimertinib or a pharmaceutically acceptable salt thereof for manufacturing a pharmaceutical composition for treatment of solid cancers.

Advantageous Effects of Invention

A combination of the present invention is useful for treatment of solid cancers.

DESCRIPTION OF EMBODIMENTS (1) Axl Inhibitor

An Axl inhibitor to be used for the combination of the present invention, in one aspect, includes N-{5-[(6,7-dimethoxy-4-quinolinyl)oxy]-2-pyridinyl}-2,5-dioxo-1-phenyl-1,2,5,6,7,8-hexahydro-3-quinolinecarboxamide represented by the following formula described in WO 2015/012298:

[Chem. 1]

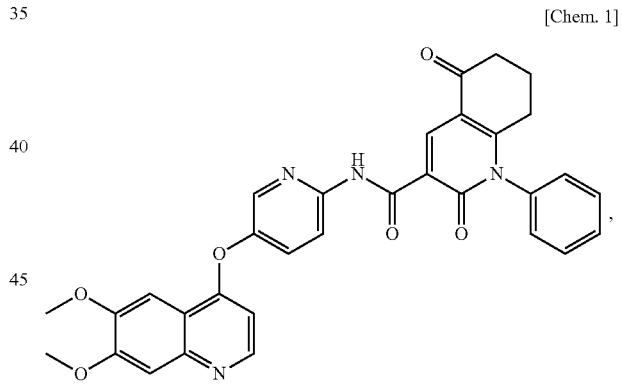

a pharmaceutically acceptable salt thereof, or a hydrate of the compound or the salt.

Further aspects of the Axl inhibitor include a compound described in International Publication WO2007/030680, WO2007/057399, WO2007/070872, WO2008/045978, WO2008/080134, WO2008/083356, WO2008/128072, WO2008/083353, WO2008/083354, WO2008/083367, WO2008/083357, WO2009/007390, WO2009/024825, WO2009/047514, WO2009/053737, WO2009/054864, WO2009/127417, WO2010/005876, WO2010/005879, WO2010/090764, WO2010/128659, WO2012/028332, WO2012/135800, WO2013/074633, WO2013/115280, WO2013/162061, WO2014/091265, WO2015/012298, WO2016/006706, WO2016/097918, WO2016/183071, WO2017/028797, WO2017/172596, or WO2018/071343.

The Axl inhibitor to be used in the combination of the present invention includes, in addition to the compound A, compounds described in Examples of WO2015/012298, a pharmaceutically acceptable salt thereof, or a hydrate of the compound or the salt. Preferable examples include (1) N-{5-[(6,7-dimethoxy-4-quinolinyl)oxy]-2-pyridinyl}-7,7-dimethyl-2,5-dioxo-1-phenyl-1,2,5,6,7,8-hexahydro-3-quinolinecarboxamide, (2) N-{5-[(6,7-dimethoxy-4-quinolinyl)oxy]-2-pyridinyl}-1-(2,2-dimethylpropyl)-2,5-dioxo-1,2,5,6,7,8-hexahydro-3-quinolinecarboxamide, (3) N-[5-({7-[3-(4-morpholinyl)propoxy]-4-quinolinyl}oxy)-2-pyridinyl]2,5-dioxo-1-phenyl-1,2,5,6,7,8-hexahydro-3-quinolinecarboxamide, (4) N-{4-[(6,7-dimethoxy-4-quinolinyl)oxy]-3-fluorophenyl}-2,5-dioxo-1-phenyl-1,2,5,6,7,8-hexahydro-3-quinolinecarboxamide, (5) N-{4-[(6,7-dimethoxy-4-quinolinyl)oxy]phenyl}-2,5-dioxo-1-phenyl-1,2,5,6,7,8-hexahydro-3-quinolinecarboxamide, (6) N-{5-[(6,7-dimethoxy-4-quinolinyl)oxy]-2-pyridinyl}-1-(4-fluorophenyl)-2,5-dioxo-1,2,5,6,7,8-hexahydro-3-quinolinecarboxamide, (7) N-{5-[(6,7-dimethoxy-4-quinolinyl)oxy]-2-pyridinyl}-1-(3-fluorophenyl)-2,5-dioxo-1,2,5,6,7,8-hexahydro-3-quinolinecarboxamide, (8) N-{5-[(6,7-dimethoxy-4-quinolinyl)oxy]-2-pyridinyl}-1-(2-fluorophenyl)-2,5-dioxo-1,2,5,6,7,8-hexahydro-3-quinolinecarboxamide, (9) N-{5-[(6,7-dimethoxy-4-quinazolinyl)oxy]-2-pyridinyl}-2,5-dioxo-1-phenyl-1,2,5,6,7,8-hexahydro-3-quinolinecarboxamide, (10) N-{5-[(6,7-dimethoxy-4-quinazolinyl)oxy]-2-pyridinyl}-1-(4-fluorophenyl)-2,5-dioxo-1,2,5,6,7,8-hexahydro-3-quinolinecarboxamide, (11) N-{5-[(6,7-dimethoxy-4-quinolinyl)oxy]-2-pyridinyl}-1-[(2S)-1-hydroxy-3-methyl-2-butanyl]-2,5-dioxo-1,2,5,6,7,8-hexahydro-3-quinolinecarboxamide, (12) N-{4-[(6,7-dimethoxy-4-quinolinyl]oxy]-3-fluorophenyl)-1-(3-fluorophenyl)-2,5-dioxo-1,2,5,6,7,8-hexahydro-3-quinolinecarboxamide, (13) N-{5-[(6,7-dimethoxy-4-quinolinyl)oxy]-2-pyridinyl}-6,6-dimethyl-2,5-dioxo-1-phenyl-1,2,5,6,7,8-hexahydro-3-quinolinecarboxamide, (14) N-[5-({6-methoxy-7-[3-(4-morpholinyl)propoxy]-4-quinolinyl}oxy)-2-pyridinyl]-2,5-dioxo-1-phenyl-1,2,5,6,7,8-hexahydro-3-quinolinecarboxamide, (15) N-{5-([7-(3-hydroxy-3-methylbutoxy)-6-methoxy-4-quinolinyl]oxy}-2-pyridinyl)-2,5-dioxo-1-phenyl-1,2,5,6,7,8-hexahydro-3-quinolinecarboxamide, or (16) N-[5-({6-methoxy-7-[3-(1-pyrrolidinyl)propoxy]-4-quinolinyl}oxy)-2-pyridinyl]-2,5-dioxo-1-phenyl-1,2,5,6,7,8-hexahydro-3-quinolinecarboxamide, a pharmaceutically acceptable salt of any one of the compounds, or a hydrate of any one of the compounds or the salts.

In the present invention, unless specifically indicated, all of the isomers are included. For example, an alkyl group includes linear and branched alkyl groups. In addition, geometrical isomers of double bonds, rings, fused rings (E-, Z-, cis-, trans-isomers), optical isomers by the presence of an asymmetric carbon atom (R-, S-isomer, α-, β-configurations, enantiomers, diastereomers), optical active isomers having optical rotation property (D, L, d, l-isomers), polar isomers by chromatographic separation (high polar isomer, low polar isomer), equilibrium compounds, rotamers, mixtures thereof at any rate, and racemic mixtures are all included in the present invention. Furthermore, the present invention also encompasses all isomers by tautomers.

Furthermore, the optical isomer of the present invention is not only limited to an optical isomer having purity of 100% but also may include other optical isomers having purity of less than 50%.

The compound A is converted into a corresponding pharmaceutically acceptable salt by a well-known method. The pharmaceutically acceptable salt is preferably water-soluble. Examples of suitable pharmaceutically acceptable salt include salts of an alkali metal (potassium, sodium, etc.), salts of an alkaline earth metal (calcium, magnesium, etc.), ammonium salts, salts of pharmaceutically acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine, N-methyl-D-glucamine, etc.), acid addition salts (inorganic acid salts (hydrochloride, hydrobromide, hydroiodide, sulfate, phosphate, nitrate, etc.), organic acid salts (acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, gluconate, etc.), and the like), and the like.

The compound A and the salt thereof can be converted into a hydrate.

Furthermore, the compound A may be labeled with an isotope thereof (for example, $^{2}H$, $^{3}H$, $^{11}C$, $^{13}C$, $^{14}C$, $^{13}N$, $^{15}N$, $^{15}O$, $^{17}O$, $^{18}O$, $^{35}S$, $^{18}F$, $^{36}Cl$, $^{123}I$, $^{125}I$, and the like).

The compound A can be produced according to Example 5 described in WO2015/012298.

The compound A, a pharmaceutically acceptable salt thereof, or a hydrate of the compound or the salt to be used in the combination of the present invention is usually administered systemically or locally and orally or parenterally. Examples of oral agents include liquid drugs for internal use (for example, elixirs, syrups, pharmaceutically acceptable water-based agents, suspensions, and emulsions), solid drugs for internal use (for example, tablets (including sublingual tablets and orally disintegrating tablets), pills, capsules (including hard capsules, soft capsules, gelatin capsules, and microcapsules), powders, granules, and lozenges), and the like. Examples of parenteral agents include liquid drugs (for example, injections (subcutaneous injections, intravenous injections, intramuscular injections, intraperitoneal injections, drip agents, etc.), eye drops (for example, aqueous eye drops (aqueous eye drops, aqueous eye drop suspensions, viscous eye drops, solubilized eye drops, etc.), nonaqueous eye drops (for example, nonaqueous eye drops, nonaqueous eye drop suspensions, etc.), and the like), agents for external use (for example, ointments (ophthalmic ointments, etc.)), ear-drops, and the like. These formulations may be controlled release agents such as rapid release formulations and sustained release formulations. These formulations can be produced by well-known methods, for example, the methods described in the Japanese Pharmacopoeia.

Liquid drugs for internal use as the oral agent can be produced by, for example, dissolving, suspending, or emulsifying an effective component in a generally used diluent (for example, purified water, ethanol, mixture liquid thereof, or the like). A liquid drug may include a wetting agent, a suspension agent, an emulsifying agent, a sweetening agent, a flavoring agent, an aromatic agent, a preservative, a buffer agent, and the like.

Solid drugs for internal use as the oral agent are formulated by, for example, mixing the effective component with a vehicle (for example, lactose, mannitol, glucose, microcrystalline cellulose, starch, and the like), a binder (for example, hydroxypropyl cellulose, polyvinylpyrrolidone, magnesium metasilicate aluminate, and the like), a disintegrant (for example, calcium carboxymethylcellulose, and the like), a lubricant (for example, magnesium stearate, and the like), a stabilizer, a dissolution adjuvant (glutamic acid, aspartic acid, and the like), and the like according to standard methods. As necessary, coating may be carried out with a coating agent (for example, saccharose, gelatin, hydroxypropyl cellulose, hydroxypropyl methyl cellulose phthalate, and the like), and coating of two or more layers may be carried out.

Agents for external use as parenteral agents are produced by well-known methods or generally used prescriptions. For example, an ointment may be produced by incorporation or melting of an effective component into a base material. The ointment base material is selected from well-known materials or generally used materials. For example, a single material or a mixture of two or more of materials are selected from higher fatty acids and higher fatty acid esters (for example, adipic acid, myristic acid, palmitic acid, stearic acid, oleic acid, adipate esters, myristate esters, palmitate esters, stearate esters, oleate esters, and the like), waxes (for example, beeswax, spermaceti, ceresin, and the like), surfactants (for example, polyoxyethylene alkyl ether phosphate esters, and the like), higher alcohols (for example, cetanol, stearyl alcohol, cetostearyl alcohol, and the like), silicone oils (for example, dimethylpolysiloxane, and the like), hydrocarbons (for example, hydrophilic petrolatum, white petrolatum, purified lanolin, liquid paraffin, and the like), glycols (for example, ethylene glycol, diethylene glycol, propylene glycol, polyethylene glycol, macrogol, and the like), vegetable oils (for example, castor oil, olive oil, sesame oil, turpentine oil, and the like), animal oils (for example, mink oil, egg yolk oil, squalane, squalene, and the like), water, absorption promoters, and anti-irritants. Furthermore, a humectant, preservative, stabilizer, antioxidant, fragrance, and the like may be included.

The injection agents as parenteral agents include solutions, suspensions, emulsions, and solid injection agents to be dissolved or suspended in a solvent during use. The injection agent is used by, for example, dissolving, suspending, or emulsifying an effective component in a solvent. Examples of the solvent include distilled water for injection, physiological saline, vegetable oils, alcohols such as propylene glycol and polyethylene glycol, ethanol, and mixtures thereof. Furthermore, the injection agent may contain a stabilizer, a dissolution aid (for example, glutamic acid, aspartic acid, and Polysorbate 80 (registered trademark), etc.), a suspending agent, an emulsifying agent, a soothing agent, a buffer, a preservative, and the like. Such an injection agent is produced by sterilizing or employing an aseptic process at the final step. Furthermore, it is also possible to employ an aseptic solid product such as a freeze-dried product produced and sterilized or dissolved in aseptic distilled water for injection or other solvents before use.

The dose of the compound A, a pharmaceutically acceptable salt thereof, or a hydrate of the compound or the salt to be used in the combination of the present invention is different depending on age, body weight, symptoms, therapeutic effects, administration methods, treatment time, and the like. However, the dosage for one adult is generally from 1 ng to 1000 mg per dose once or several times per day by oral administration, from 0.1 ng to 100 mg per dose once or several times per day by parenteral administration, or continuous administration for 1 hour to 24 hours per day intravenously. Needless to say, as mentioned above, the dose to be used varies depending on various conditions. Therefore, doses lower than the ranges specified above may be sufficient in some cases, and doses higher than the ranges specified above may be needed in some cases.

For example, a dose in one aspect is 2 mg/kg to 20 mg/kg of body weight, and preferably 2 mg/kg to 20 mg/kg of body weight per day.

(2) Osimertinib

In the present invention, osimertinib is an irreversible EGFR tyrosine kinase inhibitor selectively inhibiting the T790M gene mutation (hereinafter referred to as T790M mutation) and activating mutation of the epidermal growth factor receptor (EGFR). In Japan, osimertinib is approved as Tagrisso (registered trademark) for "EGFR T790M Mutation-positive inoperable or recurrent non-small cell lung cancer resistant to EGFR Tyrosine kinase inhibitors." Furthermore, as osimertinib, a pharmaceutically acceptable salt thereof (for example, osimertinib mesylate) may be used.

The dose of osimertinib or the pharmaceutically acceptable salt thereof to be used in the combination of the present invention is different depending on age, body weight, symptoms, therapeutic effects, administration methods, treatment time, and the like, but is adjusted such that the optimum desired effect can be exhibited.

When the osimertinib or the pharmaceutically acceptable salt thereof is used, the dose in one aspect is 0.01 to 20 mg/kg of body weight, and more preferably 0.1 to 10 mg/kg of body weight.

[Toxicity]

The combination of the present invention has sufficiently low toxicity and can be used safely as a pharmaceutical product.

[Application to Pharmaceutical Products]

One aspect of diseases treated by the combination of the present invention is solid cancers. The solid cancers related to the present invention are not particularly limited, but examples thereof include head and neck cancer, nasopharyngeal cancer, esophageal cancer, gastro-esophageal junction cancer, esophageal adenocarcinoma, stomach cancer, large-intestine cancer, colon cancer, rectum cancer, small-intestine cancer, anal cancer (for example, anal canal cancer), liver cancer (for example, hepatocellular carcinoma), gallbladder cancer, bile duct cancer, biliary tract cancer, pancreatic cancer, thyroid cancer, parathyroid cancer, lung cancer (for example, non-small cell lung cancer (for example, squamous non-small cell lung cancer, non-squamous non-small cell lung cancer), small cell lung cancer), breast cancer, ovarian cancer (for example, serous ovarian cancer, ovarian clear cell adenocarcinoma), fallopian tube cancer, uterine cancer (for example, cervical cancer, uterine body cancer, endometrial cancer), vaginal cancer, vulvar cancer, penile cancer, kidney cancer (for example, renal cell carcinoma, clear cell renal cell carcinoma), adrenal cancer, urothelial carcinoma (for example, urinary bladder cancer, upper urinary tract cancer, ureteral cancer, renal pelvic cancer, and urethral cancer), prostate cancer, testicular tumor (for example, germ cell tumor), bone and soft tissue sarcoma (for example, Ewing's sarcoma, childhood rhabdomyosarcoma, and uterine body leiomyosarcoma), skin cancer (for example, uveal malignant melanoma, malignant melanoma (for example, malignant melanoma in the skin, oral mucoepithelium or intraorbital, etc.), Merkel cell carcinoma), glioma (for example, glioblastoma, gliosarcoma), brain tumor (for example, glioblastoma), spinal tumor, Kaposi's sarcoma, squamous cell carcinoma, pleural mesothelioma, primary peritoneal cancer, endocrine cancer, childhood cancer, or cancer of unknown primary origin. Among them, for solid cancer patients for which the therapeutic effect by an Axl inhibitor or an EGFR inhibitor alone is not sufficient, the combination of the present invention can be expected to maximize its antitumor effect, in particular. Furthermore, the combination of the present invention can reduce the dose of each drug. As a result, reduction of an adverse reaction can be expected.

EGFR gene exon 19 deletion mutation-positive lung cancer of the present invention is EGFR gene mutation-positive lung cancer.

The solid cancer patients for which the therapeutic effect by an Axl inhibitor is not sufficient in the present invention include: (1) solid cancer patients with solid cancer refractory to the Axl inhibitor, or (2) patients with solid cancer that progressed during treatment or recurred after treatment with the Axl inhibitor.

The solid cancer patients for which the therapeutic effect by an EGFR inhibitor is not sufficient in the present invention include: (1) patients with solid cancer refractory to the EGFR inhibitor, or (2) patients with solid cancer that progressed during treatment or recurred after treatment with the EGFR inhibitor.

Examples of the solid cancer refractory to the EGFR inhibitor of the present invention include an EGFR inhibitor-resistant lung cancer (for example, gefitinib-resistant lung cancer), but it is not limited thereto.

In one aspect, the combination of the present invention can be applied to treatment of metastatic cancer or suppression of metastasis.

In one aspect, the combination of the present invention suppresses recurrence.

In the present invention, treatment means bringing about at least one effect among extension of progression-free survival time (PFS), extension of overall survival time (OS), extension of disease-free survival time (DFS), extension of time to progression (TTP), extension of event-free survival (EFS), extension of recurrence-free survival (RFS), reduction of a tumor size, suppression of tumor growth (retardation or stopping), suppression of tumor metastasis (retardation or stopping), suppression of recurrence (prevention or retardation), and alleviation of one or a plurality of symptoms associated with cancer.

In one aspect, the combination of the present invention is used for treatment of malignant melanoma, lung cancer, kidney cancer, pleural mesothelioma, head and neck cancer, stomach cancer, glioma, or large-intestine cancer.

The "administering in combination" in the present invention includes simultaneous administration of compounds having the same or different dosage form, or administration of compounds separately (for example, sequential administration). More specifically, "administering in combination" includes administering a form of a compounding agent including all components blended in one formulation, or administering as separate formulations. Administration as separate formulations includes simultaneous administration and administration at different times. In the administration at different times, the compound A, a pharmaceutically acceptable salt thereof, or a hydrate of the compound or the salt may be administered before osimertinib or a pharmaceutically acceptable salt thereof. Alternatively, osimertinib or the pharmaceutically acceptable salt thereof may be administered before the compound A, a pharmaceutically acceptable salt thereof, or a hydrate of the compound or the salt. Respective administration methods may be the same as or different from each other.

In the present invention, the combination of the present invention may be administered in combination with other medicine (for example, a well-known anti-cancer drug) for the purposes of: (1) supplementing and/or enhancing the therapeutic effect, (2) improving the kinetics/absorption and reducing the dose; and/or (3) reducing an adverse reaction.

In the present invention, the solid cancer patient "treated with osimertinib or a pharmaceutically acceptable salt thereof," and the solid cancer patient "treated with N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt" include both solid cancer patients treated with "osimertinib or a pharmaceutically acceptable salt thereof" or "N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt" before undergoing treatment with the other agent of the combination of the present invention and patients treated with "osimertinib, or a pharmaceutically acceptable salt thereof" or "N-{5-[(6,7-dimethoxy-4-quinolinyl)oxy]-2-pyridinyl}-2,5-dioxo-1-phenyl-1,2,5,6,7,8-hexahydro-3-quinolinecarboxamide, a pharmaceutically acceptable salt thereof, or a hydrate of the compound or the salt" during treatment with the other agent of the combination of the present invention.

EXAMPLES

Hereinafter, the present invention is described specifically with reference to Examples, but the present invention is not limited thereto.

As an Axl inhibitor, N-{5-[(6,7-dimethoxy-4-quinolinyl)oxy]-2-pyridinyl}-2,5-dioxo-1-phenyl-1,2,5,6,7,8-hexahydro-3-quinolinecarboxamide (a compound A) was used. The compound A can be produced by a well-known method, for example, a method described in Example 5 of WO2015/012298.

Biological Example: Evaluation of Antitumor Effect by Combined Use of Compound a and Osimertinib on EGFR (Epidermal Growth Factor Receptor) Gene Activating Mutation-Positive Human Lung Cancer Cell Line (In Vitro)

[Operation]
(1) Cell Culture

A human non-small cell lung cancer cell line (Immuno-Biological Laboratories Co., Ltd.) in which EGFR was abnormally activated due to deletion of exon 19 of the EGFR gene was used. Cells were subcultured in RPMI 1640 medium (hereinafter referred to as medium) including 10% inactivated fetal bovine serum and 2 mM L-glutamine under conditions of 5% $CO_2$ and 37° C.

(2) Cell Survivability Evaluation

Cells suspended in a medium were seeded in a 96 well plate at a density of $2.0 \times 10^3$ cells/100 μL per well and cultured overnight under conditions of 5% $CO_2$ and 37° C. To the culture medium of each well, osimertinib or a vehicle having four times higher concentration than the final concentration and the compound A or a vehicle having four times higher concentration than each final concentration were added each at 50 μL per well and cultured under conditions of 5% $CO_2$ and 37° C. for 72 hours. After culturing, the number of surviving cells was measured using MTT (3-(4,5-di-methylthiazol-2-yl)-2,5-diphenyltetrazolium bromide, yellow tetrazole) as a tetrazolium salt that colors by a reduction reaction of living cells.

(3) Data Analysis

The cell proliferation suppression rate (%) in each compound-treated group was calculated as a relative value when a vehicle-treated group was defined as 100%. The combination index (CI) value described in Advances in Enzyme Regulation, Vol. 22, 1984, p. 27-55 was calculated using the calculated cell proliferation suppression rate (%), and the effect of combined use of each compound was analyzed.

Note here that the CI value is an index generally used for determining the strength of the effect of combined use and that the median value (Median CI) was calculated from each CI value. It was determined that CI<1 showed a synergistic effect, CI=1 showed an additive effect, and CI>1 showed an antagonistic effect.

[Results]

Table 1 shows evaluation results of antitumor effect by treatment using a compound A and osimertinib in combination. The median value of CI when the compound A and osimertinib are used in combination is less than 0.30, showing a strong synergistic effect. From the above, it was verified that combined use of the compound A and osimertinib exhibited a strong antitumor effect.

TABLE 1

| Osimertinib (μmol/L) | Compound A (μmol/L) | CI value | Median CI value |
|---|---|---|---|
| 0.001 | 0.1 | 0.417 | 0.127 |
| 0.001 | 1 | 0.212 | |
| 0.01 | 0.1 | 0.011 | |
| 0.01 | 1 | 0.011 | |
| 0.1 | 0.1 | 0.042 | |
| 0.1 | 1 | 0.025 | |
| 1 | 0.1 | 0.479 | |
| 1 | 1 | 0.348 | |

INDUSTRIAL APPLICABILITY

The combination of the present invention exhibits a significant antitumor effect, and it is therefore useful for treatment of solid cancers.

The invention claimed is:

1. A method for treating an epidermal growth factor receptor (EGFR) inhibitor-resistant non-small cell lung cancer (NSCLC) in a subject in need thereof, comprising administering an effective amount of N-{5-[(6,7-dimethoxy-4-quinolinyl)oxy]-2-pyridinyl}-2,5-dioxo-1-phenyl-1,2,5,6,7,8-hexahydro-3-quinolinecarboxamide (compound), a pharmaceutically acceptable salt thereof, or a hydrate of the compound or the salt in combination with osimertinib or a pharmaceutically acceptable salt thereof, to the subject, wherein the EGFR inhibitor-resistant NSCLC is EGFR T790M mutation-positive NSCLC.

2. The method of claim 1, wherein the subject has been treated with osimertinib or a pharmaceutically acceptable salt thereof.

3. The method according to claim 1, wherein the EGFR inhibitor-resistant lung cancer is a gefitinib-resistant lung cancer.

* * * * *